US00PP31290P2

(12) United States Plant Patent
Gmitter, Jr.

(10) Patent No.: US PP31,290 P2
(45) Date of Patent: Dec. 31, 2019

(54) MANDARIN TREE NAMED 'UF1351'

(50) Latin Name: ***Citrus reticulata* hybrid**
Varietal Denomination: UF1351

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/998,370

(22) Filed: Aug. 8, 2018

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202
See application file for complete search history.

(56) References Cited

U.S. PATENT DOCUMENTS

| | | | |
|---|---|---|---|
| PP21,356 | P3 | 10/2010 | Gmitter et al. |
| PP26,086 | P3 | 11/2015 | Grosser |
| PP27,145 | P3 | 9/2016 | Grosser |
| PP27,581 | P2 | 1/2017 | Chaparro et al. |
| PP27,829 | P3 | 4/2017 | Grosser |
| PP29,091 | P3 | 3/2018 | Grosser |

OTHER PUBLICATIONS

U.S. Appl. No. 15/998,369, filed Aug. 8, 2018, Gmitter.

Vardi, et al., "Induction of Seedlessness in Citrus: From Classical Techniques to Emerging Biotechnological Approaches," *J Amer Soc Hort Sci* 133(1):117-126, 2008.

*Primary Examiner* — Annette H Para
(74) *Attorney, Agent, or Firm* — Dentons US LLP

(57) ABSTRACT

'UF1351' is a new and distinct hybrid cultivar of mandarin tree (*Citrus reticulata*) distinguished at least by the mid-season maturation and high quality rating of its fruit, and its significant tolerance to Huanglongbing (HLB), which is also known as citrus greening disease.

7 Drawing Sheets

Latin name of the genus and species of the plant claimed: *Citrus reticulata* hybrid.
Variety denomination: 'UF1351'.

BACKGROUND OF THE INVENTION

The present invention relates to a new and distinct hybrid cultivar of mandarin tree (*Citrus reticulata*) designated 'UF1351'. 'UF1351' can be distinguished at least by the mid-season maturation and high quality rating of its fruit, and its significant tolerance to Huanglongbing (HLB), which is also known as citrus greening disease.

'UF1351' was derived from a seedling tree that was selected from a family of hybrids that was produced by a cross performed at Lake Alfred, Fla. in the spring of 1991. The seed parent was 'LB8-9' (U.S. Pat. PP21,356), which was produced by crossing the mandarin variety 'Clementine' (unpatented) and tangelo variety 'Minneola' (unpatented). The pollen parent was the tangor cultivar 'Murcott' (unpatented), which has unknown parentage. The original seedling tree was planted in the field at Lake Alfred, Fla. in October, 1993 and was selected during the autumn of 2003. 'UF1351' was first asexually propagated in 2008 at Lake Alfred, Fla. by top working it onto existing, unreleased and unnamed citrus seedling rootstock hybrids that were growing in the field. 'UF1351' was also grafted onto unreleased seedling rootstock hybrids as well as sour orange in the greenhouse and then field-planted.

SUMMARY OF THE INVENTION

The following are characteristics of 'UF1351' when grown under normal horticultural practices in Florida.

'UF1351' exhibits mid-season fruit maturation, highly rated fruit quality, and significant tolerance to HLB.

'UF1351' differs from its parents and all other known citrus varieties. 'UF1351' trees can be readily and unambiguously distinguished from those of its parents 'LB8-9' and 'Murcott' at least based upon growth habit; the time of year during which their fruit matures; fruit shape and seed content; juice acidity; ease with which the peel can be removed; and disease tolerance. The trees of 'UF1351' display a moderately vigorous growth habit that tends toward a spreading canopy structure. The trees of 'LB8-9' display a very vigorous growth habit, with an upright and then spreading canopy structure. The trees of 'Murcott' display a moderately vigorous growth habit that tends toward an upright canopy structure. The fruit of 'UF1351' matures during mid-November through early January; whereas the fruit of 'LB8-9' and 'Murcott' mature during late November through late December and late January through March, respectively. The fruit of 'UF1351' is seeded in the presence of cross-pollination and exhibits an oblate to spheroid shape with a less conspicuous neck at the stem end of some fruit. The fruit of 'LB8-9' is seeded though it approaches seedlessness with restricted cross-pollinations and exhibits a spheroid to pyriform shape usually with a conspicuous neck at the stem end. The fruit of 'Murcott' is seeded even in the absence of cross-pollination and exhibits an oblate shape with no conspicuous neck. The fruit of 'UF1351' is very easy to peel; whereas, that of 'LB8-9' and 'Murcott' are moderately easy to peel though difficult to remove at the blossom end of the fruit and moderately difficult to peel, respectively. The juice produced by 'UF1351', 'LB8-9', and 'Murcott' exhibits moderate, high, and low acidity, respectively. The trees of 'UF1351', 'LB8-9', and 'Murcott' are moderately tolerant, very tolerant, and very sensitive to HLB, respectively. The trees of 'UF1351', 'LB8-9', and 'Murcott' are tolerant, very tolerant, and very sensitive to Alternaria brown spot, respectively.

'Ponkan' mandarin (unpatented) is a known variety that matures in the same season as 'UF1351'; however, trees of 'UF1351' can be readily and unambiguously distinguished from those of 'Ponkan' at least based upon growth habit, the degree to which the peel is attached to the fruit, sensitivity to HLB, and nucellar embryony. The trees of 'Ponkan' exhibit an upright growth habit; whereas, the tress of 'UF1351' exhibit a more spreading growth habit. The fruit of 'Ponkan' is much easier to peel than that of 'UF1351'. Unlike the fruit of 'UF1351', the fruit of 'Ponkan' appear puffy because its peel will separate from the fruit while it is still on the tree. Trees of 'UF1351' are substantially more tolerant to HLB than trees of 'Ponkan' that are recognized by citrus pathologists as an indicator variety for HLB. Also, the seeds produced by 'Ponkan' and 'UF13-51' are polyembronic and monoembryonic, respectively.

'Sunburst' mandarin (unpatented) is a known variety that also matures in the same season as 'UF1351'. While these two varieties also exhibit a similar growth habit and similar fruit appearance, they can be readily and unambiguously distinguished at least based upon the degree to which the peel is attached to the fruit, sensitivity to HLB, and nucellar embryony. Unlike the fruit of 'UF1351', the fruit of 'Sunburst' do not peel well. The tress of 'Sunburst' are more sensitive to HLB than those of 'UF1351'. Also, the seeds produced by 'Sunburst' are polyembryonic.

BRIEF DESCRIPTION OF THE DRAWINGS

This new hybrid mandarin tree is illustrated by the accompanying photographs captured in 2009 (FIGS. 1-6) and 2018 (FIG. 7), which show a tree's typical form, foliage, fruit, and seeds. The colors shown are as true as can be reasonably obtained by conventional photographic procedures.

DETAILED BOTANICAL DESCRIPTION

Figure 1:
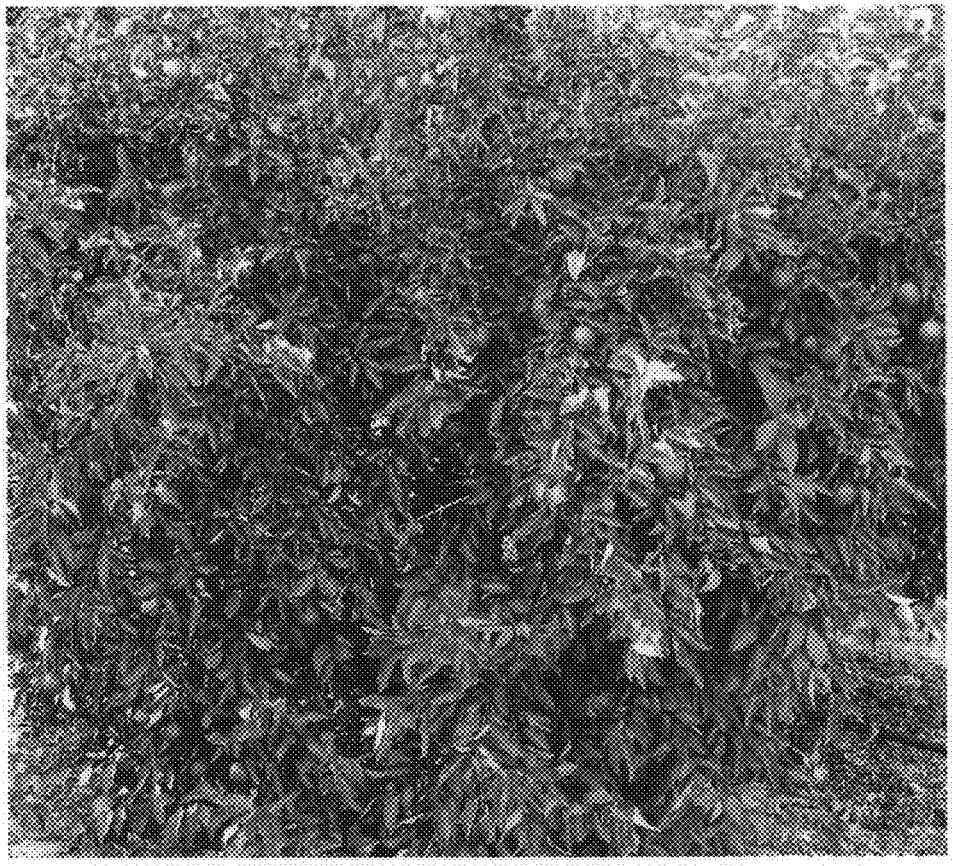
FIG. 1—Shows the overall habit of an approximately 16-year-old 'UF1351' tree in early October, which is prior to fruit maturity.
Figure 2:
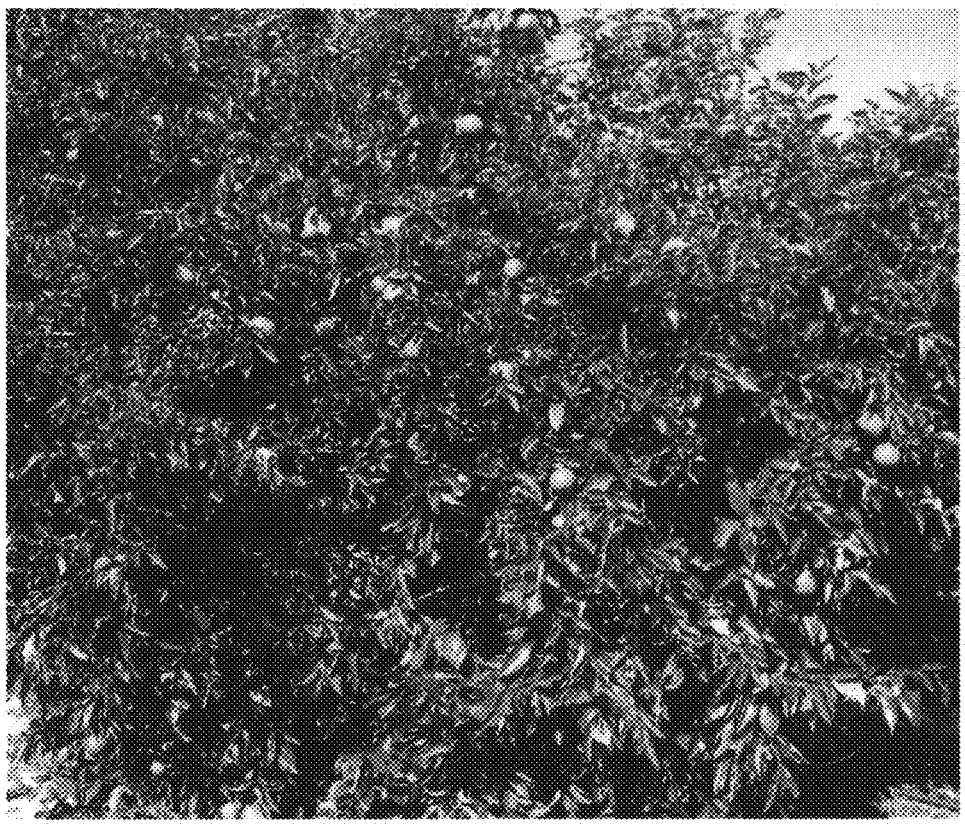
FIG. 2—Shows the overall habit of an approximately 16-year-old 'UF1351' tree in in mid-November, which is when the fruit has begun to develop color and mature.
Figure 3:
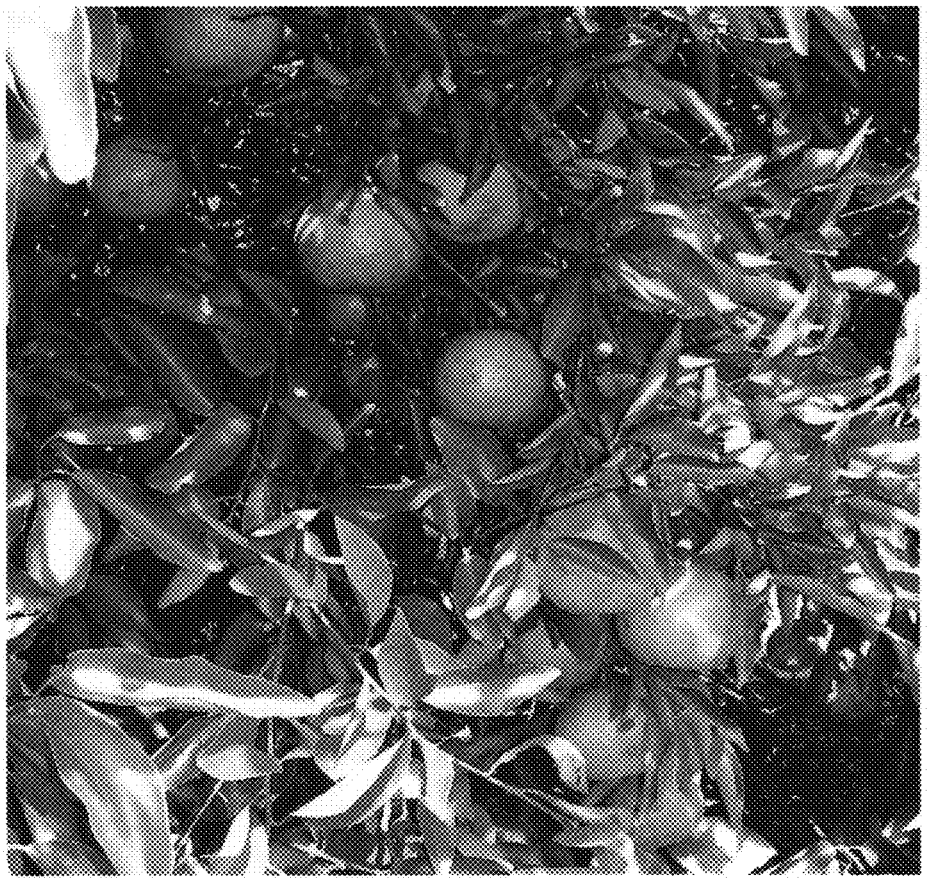
FIG. 3—Shows a close-up of the fruit-bearing habit within the canopy of an approximately 16-year-old 'UF1351' tree during mid-November.
Figure 4:
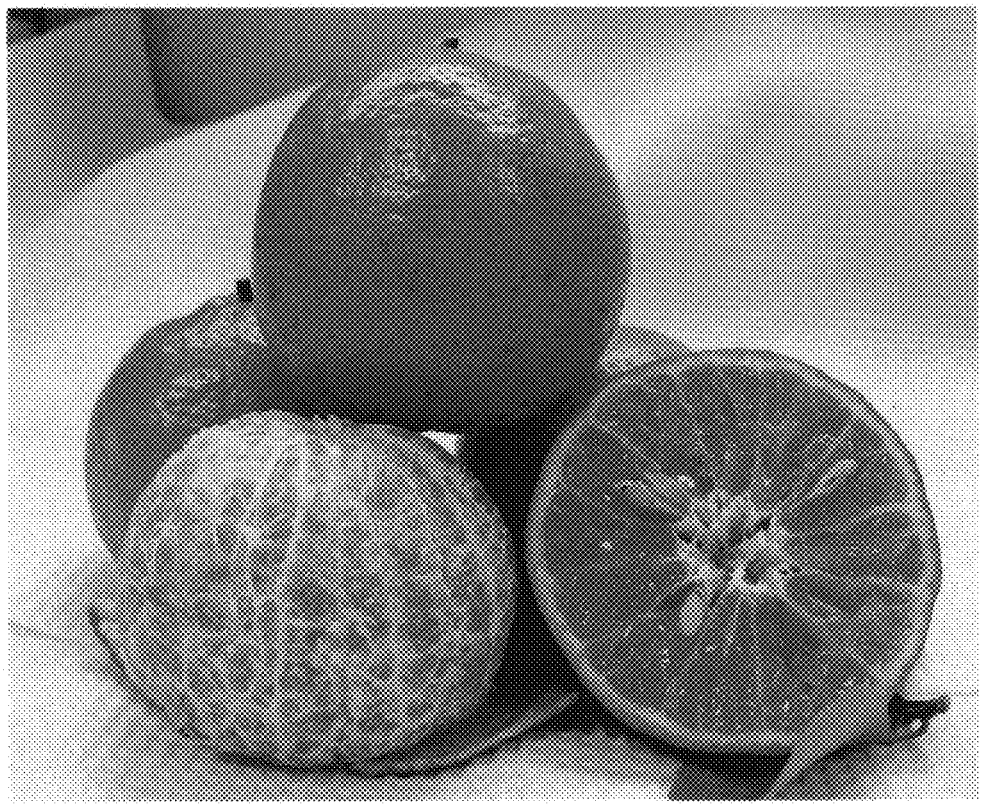
FIG. 4—Shows a close-up of fruit, with and without the rind, that were obtained from an approximately 16-year-old 'UF1351' tree, and this fruit is very mature as it had been held on the tree until late March.
Figure 5:
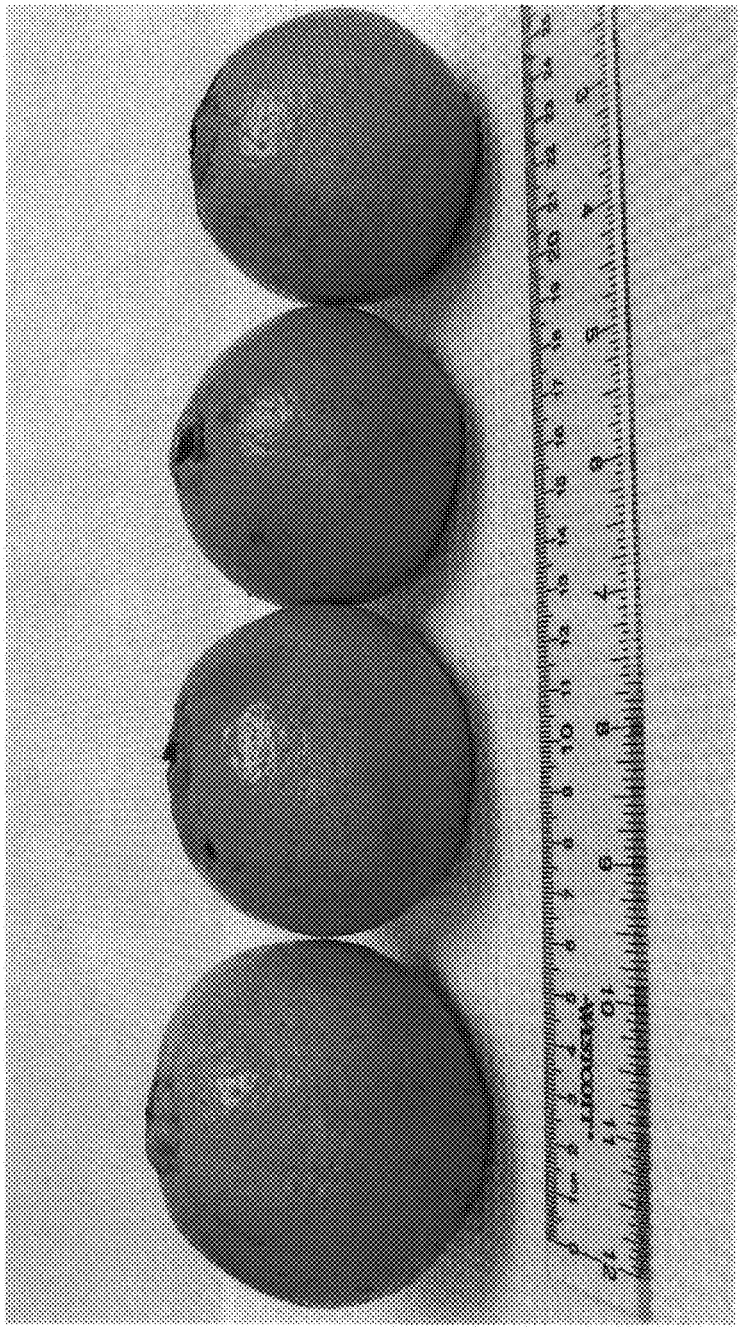
FIG. 5—Shows a close-up of mature fruit, with the rind present, that were obtained from an approximately 16-year-old 'UF1351' tree.
Figure 6:
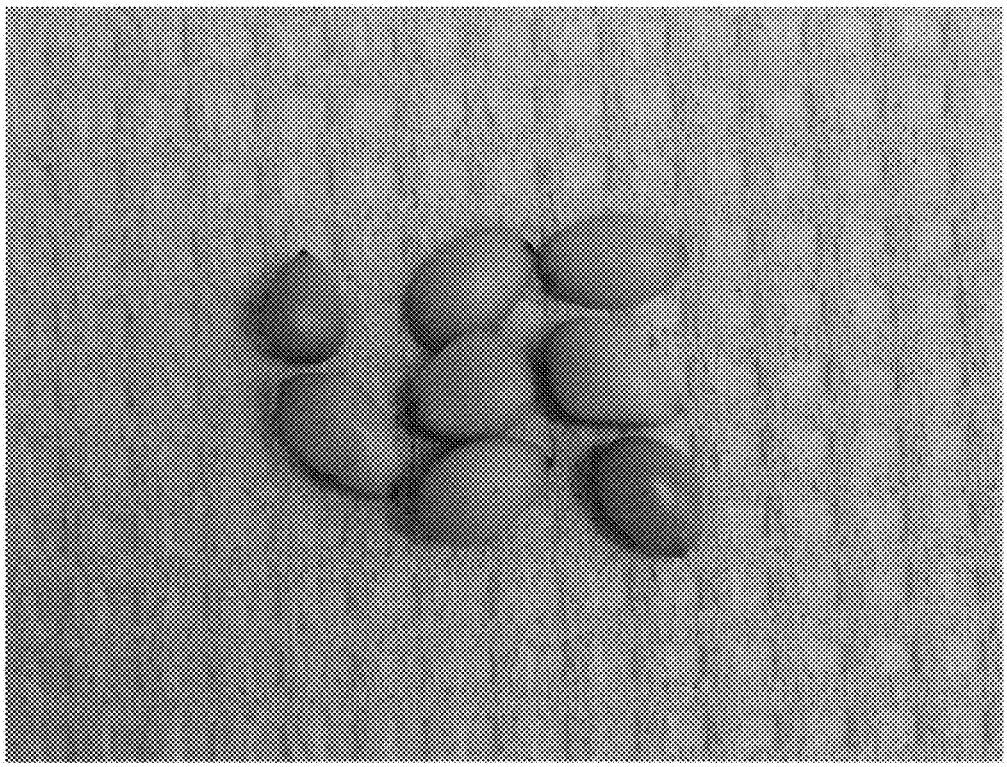
FIG. 6—Shows a close-up of mature monoembryonic 'UF1351' seeds with different cotyledon colors that were obtained from fruit that was produced by an approximately 16-year-old tree.
Figure 7:
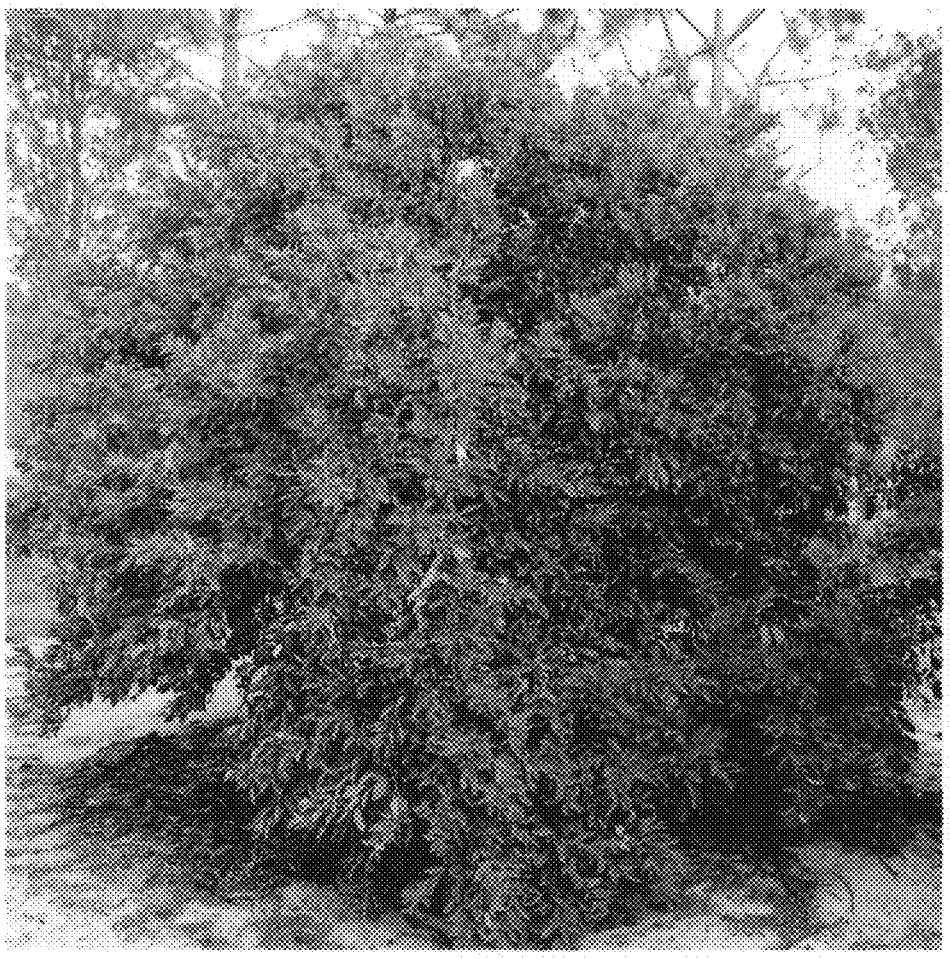
FIG. 7—Shows a 10-year-old 'UF1351' topworked tree displaying good condition although affected by HLB.

The following detailed description sets forth distinctive characteristics of 'UF1351'. The data that define these characteristics were collected from a 16-year-old tree growing on its own roots at Lake Alfred, Fla. 'UF1351' has not been observed under all possible environmental conditions, and the measurements given may vary when grown in different environments. Further, certain characteristics may vary with plant age. Color descriptions, except those recited in common terms, are based on The Royal Horticultural Society (R.H.S.) Colour Chart, 2nd Edition, which was published in London by The R.H.S. in association with Flower Council of Holland. If any R.H.S. color designations below differ from the accompanying photographs, the R.H.S. color designations are accurate.

Classification:

*Botanical.*—*Citrus reticulata* hybrid.

*Common name.*—Mandarin hybrid or Tangerine.

Parentage:

*Female parent.*—'LB8-9' mandarin hybrid.

*Male parent.*—'Murcott' tangor.

Tree:

*Ploidy.*—Diploid.

*Size.*—Large, with an un-pruned height of 3.35 m.

*Vigor.*—Very vigorous, growing shoots of 40-50 cm from strong spring flush on mature trees.

*Density.*—Canopies are quite dense.

*Form.*—The shape of the tree is round and drooping with most of the lateral growing branches and fewer upright growing branches at top of the canopy. Tending toward medium angles after fruit has commenced.

*Growth habit* (*current season*).—Drooping.

Trunk and Branches:

*Trunk texture.*—Smooth.

*Trunk bark color.*—RHS 197A (greyed-green) and irregularly striated with RHS N189A (greyed-green).

*Branch texture.*—Relatively smooth and without thorns or spines.

*Branch color* (*shoots from previous flush, hardened and* 4-5 *mm in diameter*).—RHS 137A (green).

Leaves:

*Size* (*lamina average*).—Length: 97 mm. Width: 50 mm. L/W ratio: 1.94 to 2.0.

*Thickness.*—Regular and average for commercial mandarin hybrids.

*Type.*—Simple.

*Shape.*—Elliptical.

*Apex.*—Retuse.

*Base.*—Acute to sub-obtuse.

*Margin.*—Entire, slightly undulate.

*Surface.*—Upper surface: Glabrous. Lower surface: Medium veins that are pinnately netted.

*Color.*—Upper surface (adaxial): RHS 143A (green). Lower surface (abaxial): RHS 143C (green).

*Petiole.*—Shape: Brevipetiolate (shorter than leaf lamina) and the junction between petiole and lamina is articulate. Width (petiole wing): Very narrow. Shape (petiole wing): Obovate. Length: 15-20 mm. Width: 3 mm. Color: RHS 143A (green).

Flowers:

*Type.*—Hermaphrodite.

*Petals.*—Number: 4-5. Color: RHS 155B (white) with yellow-green (RHS 150A) spots distribution. Length: 19-21 mm. Width: 7 mm. Calyx: Medium size. Blossom period: Late February through March in central Florida. Fragrance: Fragrant compared to other citrus blossoms.

Reproductive Organs:

*Fertility.*—Self-fertile.

*Stamen number.*—4 per petal.

*Anther color.*—RHS 13C (yellow).

*Anther filament length.*—Shorter relative to stigma.

*Pollen amount.*—Abundant.

*Pollen color* (*general*).—RHS 13A (bright-yellow).

Fruit:

*Size.*—Relatively uniform, size range from 62-72 mm in diameter, fruit height ranges from 55-65 mm.

*Shape.*—Oblate to spheroid.

*Shape* (*cross-section*).—Round.

*Apex.*—Shallow concave with rough peel surface.

*Base.*—Slight convex with short neck, wrinkled peel surface.

*Maturity.*—Mid-November to late December for commercial harvest and can be held on the tree in good condition through April for home garden use.

Rind:

*Adherence.*—Albedo (mesocarp) to flesh (endocarp) is medium low.

*Thickness.*—Medium thin with 2.5-3.0 mm thickness.

*Texture.*—Medium firm.

*Color.*—Flavedo (epicarp): Ranges from RHS N25C (orange) to RHS N25B (orange). Albedo (mesocarp): RHS 23C (yellow-orange).

*Stylar end.*—Closed.

Flesh:

*Average number of segments.*—12-13 segments per fruit.

*Segment walls.*—Soft, with sufficient strength to maintain integrity as separated.

*Juice.*—Abundant.

*Color.*—Uniformly RHS N25A (orange).

*Texture.*—Soft.

*Vesicles.*—Medium thick, with average of 13 mm in length and 2-3 mm in width.

*Eating quality.*—Soluble solids (average): 12.9 Brix. Acidity (average): 0.87%. Ratio: 14.8.

Seeds:

*Type.*—Monoembryonic.

*Number.*—Ranges from 20-28.

*Shape.*—Mostly with smooth surface, most of seeds with clavate/club shape and fewer with deltoid shape.

*Size.*—Length: 10-12 mm. Width: 6-8 mm.

*Seed coat color.*—Outer Surface: RHS NN155A (white). Inner surface: RHS 165D (greyed-orange).

*Cotyledon color.*—RHS NN155A (greyed-yellow) to RHS 193B (greyed-green).

What is claimed is:

1. A new and distinct hybrid cultivar of mandarin tree (*Citrus reticulata*) named 'UF1351', as illustrated and described herein.

* * * * *